(12) United States Patent
Choi et al.

(10) Patent No.: US 9,820,701 B2
(45) Date of Patent: Nov. 21, 2017

(54) X-RAY TARGETING DEVICE

(71) Applicant: LINKOPTICS CO., LTD., Gwangju (KR)

(72) Inventors: Yong Won Choi, Gwangju (KR); Hyo Gi Seo, Suncheon (KR); Keum Yeon Choi, Gwangju (KR); Joon Seok Lee, Gwangju (KR)

(73) Assignee: LINKOPTICS CO., LTD., Gwangju (KR)

( * ) Notice: Subject to any disclaimer, the term of this patent is extended or adjusted under 35 U.S.C. 154(b) by 80 days.

(21) Appl. No.: 14/943,149

(22) Filed: Nov. 17, 2015

(65) Prior Publication Data

US 2016/0213338 A1 Jul. 28, 2016

(30) Foreign Application Priority Data

Jan. 27, 2015 (KR) ........................ 10-2015-0013073
Oct. 13, 2015 (KR) ........................ 10-2015-0142985

(51) Int. Cl.
*A61B 6/08* (2006.01)
*A61B 6/10* (2006.01)
*A61B 6/00* (2006.01)

(52) U.S. Cl.
CPC ................ *A61B 6/08* (2013.01); *A61B 6/107* (2013.01); *A61B 6/4441* (2013.01)

(58) Field of Classification Search
CPC ........... A61B 6/08; A61B 6/48; A61B 6/5876; A61B 2034/107; A61B 5/509; A61B 90/13
USPC ................. 378/204, 205, 206, 166, 63, 170; 600/426, 407, 427, 130
See application file for complete search history.

(56) References Cited

U.S. PATENT DOCUMENTS 5,068,887 A * 11/1991 Hughes ................ G03B 42/042
378/170
2010/0246777 A1* 9/2010 Thompson ............... A61B 6/08
378/206

\* cited by examiner

*Primary Examiner* — Don Wong
(74) *Attorney, Agent, or Firm* — Lex IP Meister, PLLC (57) ABSTRACT

The present invention relates to an X-ray targeting device which includes a frame installed at an X-ray generator of an X-ray imaging device which outputs X-rays toward a patient to be measured, and a light radiation unit installed at the frame, and radiating guide light in accordance with a direction in which the X-rays are output to display a radiated position or radiated range of the X-rays with respect to the patient. According to the present invention, since an X-ray targeting device includes a light radiation unit radiating guide light in accordance with a radiated direction of X-rays, a worker can easily identify the radiated direction or the radiated range of the X-rays, thereby saving time and effort required for X-ray imaging.

5 Claims, 10 Drawing Sheets

X-RAY TARGETING DEVICE

BACKGROUND

1. Field of the Invention

The present invention relates to an X-ray targeting device, and more particularly, to an X-ray targeting device which generates guide light to display a radiated direction or a radiated range of X-rays outputted from an X-ray generator.

2. Discussion of Related Art

An X-ray imaging device is widely used as a medical device for taking an X-ray image of an internal structure of an object such as a patient or an animal.

As disclosed in Korean Patent Registration No. 10-1158100, a conventional X-ray imaging device used a method of taking an image of an internal structure of an object using a photosensitive film which is sensitive to radiation which has been radiated from an X-ray generator and passed through the object.

However, X-rays radiated from the X-ray generator cannot be identified by a worker with the naked eye, and has a difficulty in determining a radiated position or a radiated range of X-rays with respect to a patient to be measured.

SUMMARY OF THE INVENTION

The present invention has been devised to improve the above problem, and is directed to providing an X-ray targeting device which includes a light radiation unit for radiating guide light in accordance with a direction of X-rays radiated from an X-ray generator.

To achieve the above aspect, according to the present invention, an X-ray targeting device includes a frame installed at an X-ray generator of an X-ray imaging device which outputs X-rays toward a patient to be measured, and a light radiation unit installed at the frame, and radiating guide light in accordance with a direction in which the X-rays are output to display a radiated position or radiated range of the X-rays with respect to the patient.

The light radiation unit may include a housing installed at the frame, having an inner space provided inside, and having an opening, which comes in communication with the inner space, formed at a side surface facing the patient, a laser generator inserted into the inner space and radiating the guide light through the opening, and a restraining unit installed at the housing, supporting the laser generator to prevent the laser generator from being separated from the housing, and being able to change a supported state of the laser generator with respect to the housing to be able to adjust a direction in which the guide light is radiated.

The restraining unit may include a plurality of restraining members respectively installed at inner surfaces of the housing which face each other with respect to a center line of the opening to move back and forth toward and from the inner space to have end portions come in contact with the laser generator inserted into the inner space, first adjustment parts provided at the restraining members and the housing, and adjusting protruding lengths of pressing members from the inner surfaces of the housing to enable the restraining members to grip the laser generator, a plurality of the pressing members respectively installed at inner surfaces of the housing at positions apart from the restraining members in accordance with a longitudinal direction of the center line of the opening to move back and forth toward and from the inner space, and second adjustment parts provided at the restraining members and the housing, and adjusting the protruding lengths of the pressing members from the inner surfaces of the housing to be able to tilt the laser generator restrained by the restraining members by a predetermined angle.

Preferably, the plurality of the pressing members may be installed to be apart from each other in accordance with a circumferential direction at the inner surfaces of the housing.

The restraining members may have the end portions, which come in contact with the laser generator, formed in semi-spherical shapes to enable the laser generator to be supported to be easily tilted by the pressing members, and the laser generator may have insertion grooves formed in semi-spherical shapes to correspond to the end portions of the restraining members to have the restraining members respectively inserted into outer circumferential surfaces at positions facing the restraining members.

Preferably, the frame may have a through-hole formed to enable the X-rays output from the X-ray generator to pass therethrough, and a plurality of the light radiation units may be installed at the frame to be spaced apart from each other with respect to a center of the through-hole in accordance with a circular virtual line having a greater diameter than an inner diameter of the through-hole.

Meanwhile, the X-ray targeting device according to the present invention may further include a shielding member installed to surround an inner surface of the through-hole, and shielding the X-rays radiated toward an inner surface of the frame to limit the radiated range of the X-rays output from the X-ray generator.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, an X-ray targeting device according to preferred embodiments of the present invention will be described in more detail with reference to the attached drawings.

Figure 1:
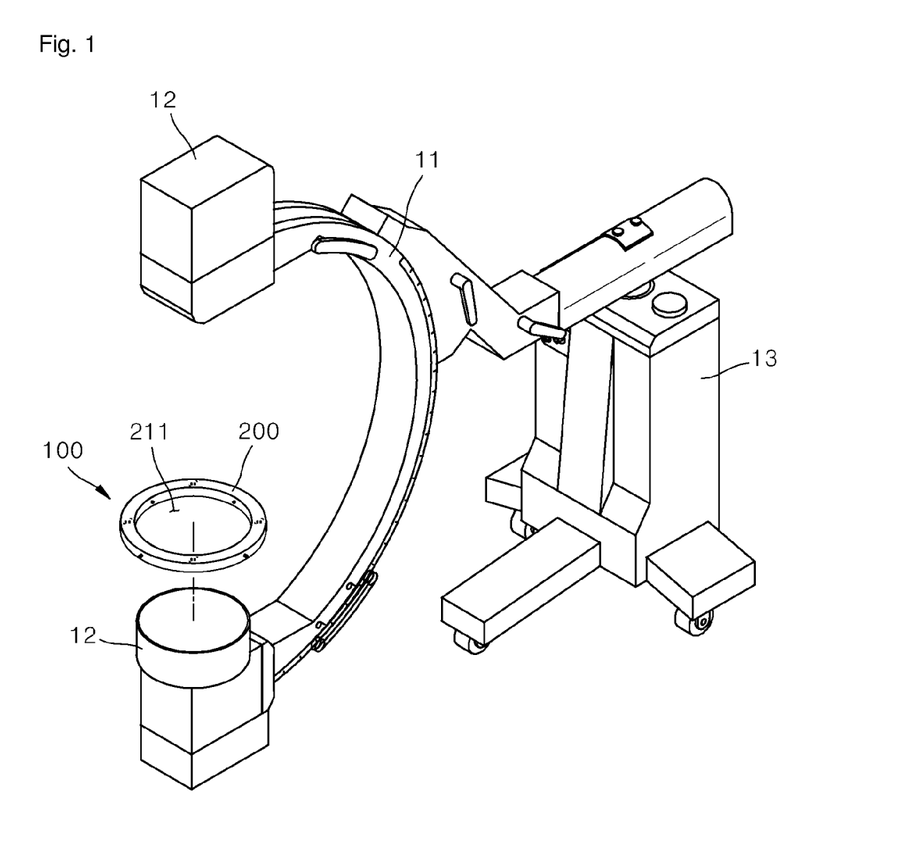
FIG. 1 is a perspective view of an X-ray targeting device according to the present invention.
Figure 2:
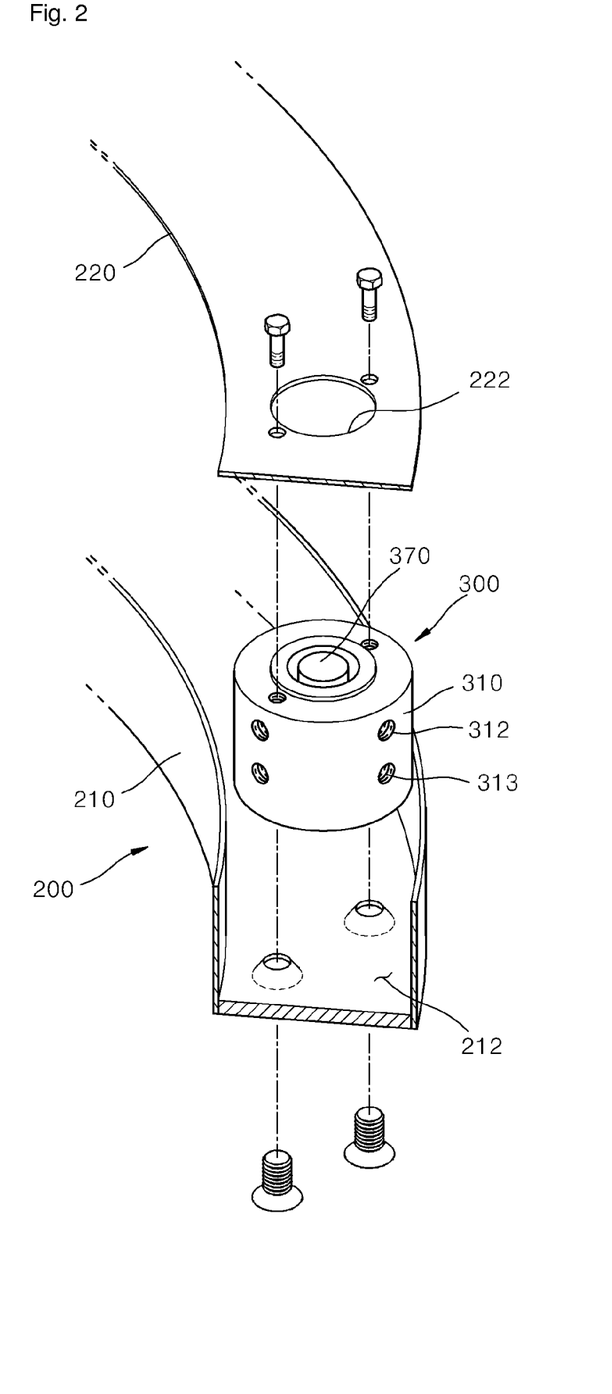
FIG. 2 is an exploded perspective view of the X-ray targeting device in FIG. 1.
Figure 3:
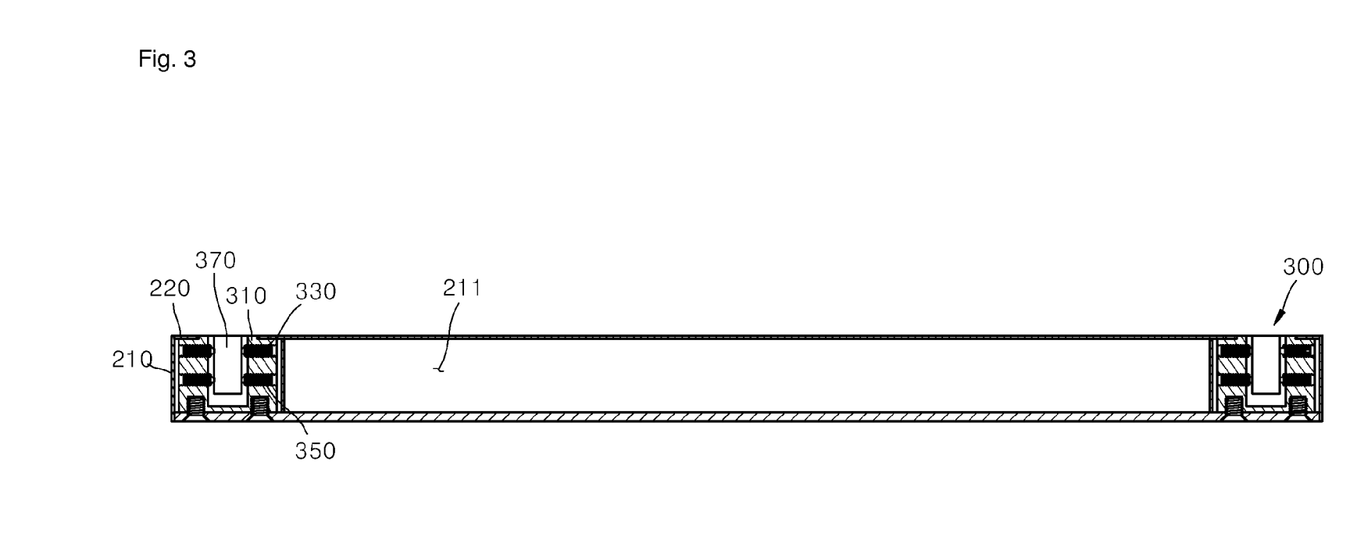
FIG. 3 is a cross-sectional view of the X-ray targeting device in FIG. 1.
Figure 4:
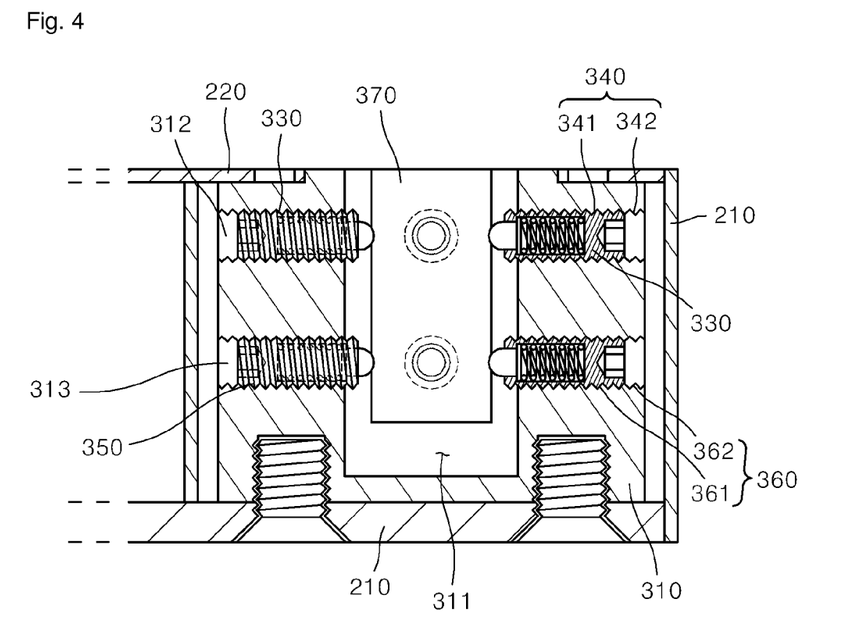
FIG. 4 is a cross-sectional view of a light radiation unit of the X-ray targeting device in FIG. 1.

An X-ray imaging device 10 at which an X-ray targeting device according to the present invention is installed is illustrated in FIG. 1, and an X-ray targeting device 100 according to a first embodiment of the present invention is illustrated in FIG. 2 to FIG. 4.

According to the present invention, the X-ray imaging device 10 at which the X-ray targeting device 100 is installed includes a support member 11 formed in a semi-spherical shape to provide a space portion in which a patient to be measured is positioned, a plurality of X-ray generators 12 installed at both end portions of the support member 11 to radiate X-rays to the space portion, and a main body 13 at which the support member 11 is rotatably installed. When taking an X-ray image, the main body 13 is moved or the support member 11 is rotated to enable the patient to be measured to be positioned at the space portion. Next, a photosensitive film which is sensitive to X-rays is positioned at the patient's body corresponding to a range to be measured, and the X-ray generators 12 which face the photosensitive film with respect to the patient are operated to take the X-ray image.

Meanwhile, detailed description of the X-ray targeting device 100 according to the first embodiment of the present invention which is installed at the X-ray generators 12 of the X-ray imaging device 10 is as follows.

Referring to the drawings, the X-ray targeting device 100 includes a frame 200 installed at the X-ray generators 12 by a fixing unit, and light radiation units 300 installed at the frame 200 and radiating guide light in accordance with a direction in which the X-rays are output to display a radiated position or a radiated range of the X-rays with respect to the human body.

The frame 200 includes a through-hole 211 formed at the center to enable the X-ray generators 12 to penetrate therethrough, a case 210 in which a ring-shaped installation space 212 is provided and having an opened upper surface, and a cover 220 installed at the case 210 to close an upper portion of the case 210.

The case 210 is formed in a ring shape having a predetermined radius with respect to the center of the through-hole 211, and has the ring-shaped installation space 212 provided to have a plurality of light radiation units 300 installed therein.

The cover 220 is formed in a ring shape corresponding to the case 210 to be able to close the opened upper surface of the case 210. Here, the cover 220 includes a vertically penetrated radiation hole 222 formed such that the guide light may be radiated from the light radiation units 300 installed at the installation space 212 of the case 210.

The fixing unit includes four fixing bolts (not shown) installed at the case 210 to be penetrated. The fixing bolts are installed to be penetrated in accordance with a radial direction of the case 210 to have end portions inserted into the through-hole 211. Preferably, the fixing bolts are installed to be spaced apart from each other in accordance with the circumferential direction. When the X-ray generators 12 are inserted into the through-hole 211, the fixing bolts are bolted at outer circumferential surfaces of the X-ray generators 12 to fix the case 210 to the X-ray generators 12.

The plurality of light radiation units 300 are installed at the installation space 212 of the case 210, and are installed to be spaced apart from each other in accordance with the circumferential direction of the case 210. The light radiation units 300 include a housing 310 installed at the frame 200, having an inner space 311 provided inside, and having an opening, which comes in communication with the inner space 311, formed at a side surface facing the human body,
a laser generator 370 inserted into the inner space 311 and radiating the guide light through the opening, and a restraining unit 320 installed at the housing 310, supporting the laser generator 370 to prevent the laser generator 370 from being separated from the housing 310, and being able to change a supported state of the laser generator 370 with respect to the housing 310 to be able to adjust a direction in which the guide light is radiated.

The housing 310 is formed in a cylindrical shape having a predetermined external diameter, and is bolted and fixed to the case 210 by the plurality of bolts. Here, it is preferable that the housing 310 be installed such that the opening comes in communication with the radiation hole 222.

In addition, at the housing 310, four first installation holes 312 are spaced apart and formed in accordance with the circumferential direction to have restraining members 330 of the restraining unit 320 coming in communication with the inner space 311 and to be described below inserted thereinto. Here, it is preferable that the first installation holes 312 be formed such that a pair of the first installation holes 312 are positioned to face each other with respect to the center of the opening, and formed to be penetrated in a radial direction of the housing 310. Meanwhile, the number of the first installation holes 312 is not limited to the illustrated example, and may be three or less, or five or more in accordance with a size of the laser generator 370.

In addition, at the housing 310, four second installation holes 313 are spaced apart and formed in accordance with the circumferential direction to have pressing members 350 of the restraining unit 320 coming in communication with the inner space 311 and to be described below inserted thereinto. Here, it is preferable that the second installation holes 313 be provided at positions spaced apart from the first installation holes 312 in accordance with a longitudinal direction of a center line of the opening, be formed such that a pair of the second installation holes 313 are positioned to face each other with respect to the center of the opening, and be formed to be penetrated in the radial direction of the housing 310. Meanwhile, the number of the second installation holes 313 is not limited to the illustrated example, and may be three or less, or five or more in accordance with the size of the laser generator 370.

The laser generator 370 is inserted into the inner space 311 of the housing 310, and radiates guide light toward the outside of the housing 310 though the opening of the housing 310. Here, it is preferable that the laser generator 370 generate a laser beam of a certain color such as red or green as the guide light to improve visibility.

Meanwhile, the laser generator 370 includes semi-spherical insertion grooves (not shown) respectively formed at outer circumferential surfaces at positions facing the first installation holes 312 and the second installation holes 313 when being inserted into the inner space 311.

The restraining unit 320 includes four restraining members 330 respectively installed at inner surfaces of the housing 310 which face each other with respect to a center line of the opening to move back and forth toward and from the inner space 311 to have end portions come in contact with the laser generator 370 inserted into the inner space 311, first adjustment parts 340 provided at the restraining members 330 and the housing 310, and adjusting protruding lengths of the pressing members 350 from the inner surfaces of the housing 310 to enable the restraining members 330 to grip the laser generator 370, the four pressing members 350 respectively installed at inner surfaces of the housing 310 at positions apart from the restraining members 330 in accordance with a longitudinal direction of the center line of the opening to move back and forth toward and from the inner space 311, and second adjustment parts 360 provided at the restraining members 330 and the housing 310, and adjusting the protruding lengths of the pressing members 350 from the inner surfaces of the housing 310 to be able to tilt the laser generator 370 restrained by the restraining members 330 by a predetermined angle.

Preferably, the restraining members 330 are installed at the first installation holes 312 of the housing 310, and are installed at the housing 310 to have one end portions thereof positioned in the inner space 311 of the housing 310.

Although not illustrated in the drawings, the restraining members 330 include a first main body installed at the first installation holes 312, a first protruding member slidably installed at the first main body in accordance with the longitudinal direction of the first installation holes 312, and a ball plunger at which a first spring for elastically biasing the first protruding member toward the center of the inner space 311 is provided. At the first main body, a first through-hole is formed at one side surface facing the laser generator 370 to enable the first protruding member to protrude therethrough, and the first protruding member is slidably installed at the first main body. A first protrusion portion which protrudes to prevent the first protruding member from passing through the first through-hole is formed at one side of the first protruding member inserted into the first main body, such that a protruding length in which the first protruding member protrudes from the first main body is limited. In addition, it is preferable that the other end portion of the first protruding member which protrudes to the outside of the first main body and is inserted into the insertion grooves of the laser generator 370 be formed in a semi-spherical shape such that the laser generator 370 may be supported to be easily tilted by the pressing members 350.

The first adjustment parts 340 include a first screw thread 341 formed at an outer circumferential surface of the first main body of the restraining members 330, and a second screw thread 342 formed at an inner circumferential surface of the first installation holes 312 of the housing 310 such that the first main body and the housing 310 can be coupled by a screw. Here, a first coupling hole is formed at the first adjustment parts 340 to enable a tool such as a driver to be coupled to another side surface of the first main body of the restraining members 330. Although not illustrated in the drawings, it is preferably that the first coupling hole be formed in a "–"shape or a "+" shape. A worker couples the tool such as a driver to the first coupling hole and rotates the first main body of the restraining members 330 to adjust the protruding lengths of the restraining members 330 with respect to the inner space 311.

Preferably, the pressing members 350 are installed at the second installation holes 313 of the housing 310, and are installed at the housing 310 to have one end portions thereof positioned at the inner space 311 of the housing 310.

Although not illustrated in the drawings, the pressing members 350 include a second main body installed at the second installation holes 313, a second protruding member slidably installed at the second main body in accordance with the longitudinal direction of the second installation holes 313, and a ball plunger at which a second spring for elastically biasing the second protruding member toward the center of the inner space 311 is provided. At the second main body, a second through-hole is formed at one side surface facing the laser generator 370 to enable the second protruding member to protrude therethrough, and the second protruding member is slidably installed at the second main body. A second protrusion portion which protrudes to prevent the second protruding member from passing through the second through-hole is formed at one side of the second protruding member inserted into the second main body, such that a protruding length in which the second protruding member protrudes from the second main body is limited. In addition, it is preferable that the other end portion of the second protruding member which protrudes to the outside of the second main body and is inserted into the insertion grooves of the laser generator 370 be formed in a semi-spherical shape.

The second adjustment parts 360 include a third screw thread 361 formed at an outer circumferential surface of the second main body of the pressing members 350, and a fourth screw thread 362 formed at an inner circumferential surface of the second installation holes 313 of the housing 310 such that the second main body and the housing 310 can be coupled by a screw. Here, a second coupling hole is formed at the second adjustment parts 360 to enable the tool such as a driver to be coupled to another side surface of the second main body of the pressing members 350. Although not illustrated in the drawings, it is preferably that the second coupling hole be formed in a "–"shape or a "+" shape. The worker couples the tool such as a driver to the second coupling hole and rotates the second main body of the pressing members 350 to adjust the protruding lengths of the pressing members 350 with respect to the inner space 311.

Detailed description of a method of assembling the above-mentioned light radiation units 300 is as follows. First, install the restraining members 330 and the pressing members 350 at the first installation holes 312 and the second installation holes 313 of the housing 310 such that one end portions of the restraining members 330 and the pressing members 350 protrude toward the inner space 311 of the housing 310. Next, the laser generator 370 is inserted into the inner space 311 of the housing 310, the protruding lengths of the restraining members 330 are adjusted, and the laser generator 370 is fixed to the housing 310. Here, when making a radiated direction of the guide light adjacent to or spaced apart from a direction of the center of the through-hole 211 of the frame 200, the protruding lengths of the pressing members 350 with respect to the inner surfaces of the housing 310 are adjusted to set the laser generator 370 to be tilted.

The X-ray targeting device 100 according to the present invention which is configured as above includes the light radiation units 300 which radiate guide light in accordance with a radiated direction of X-rays, such that a worker can easily identify the radiated direction or a radiated range of the X-rays, and time and effort required for X-ray imaging may be saved.

Figure 5:
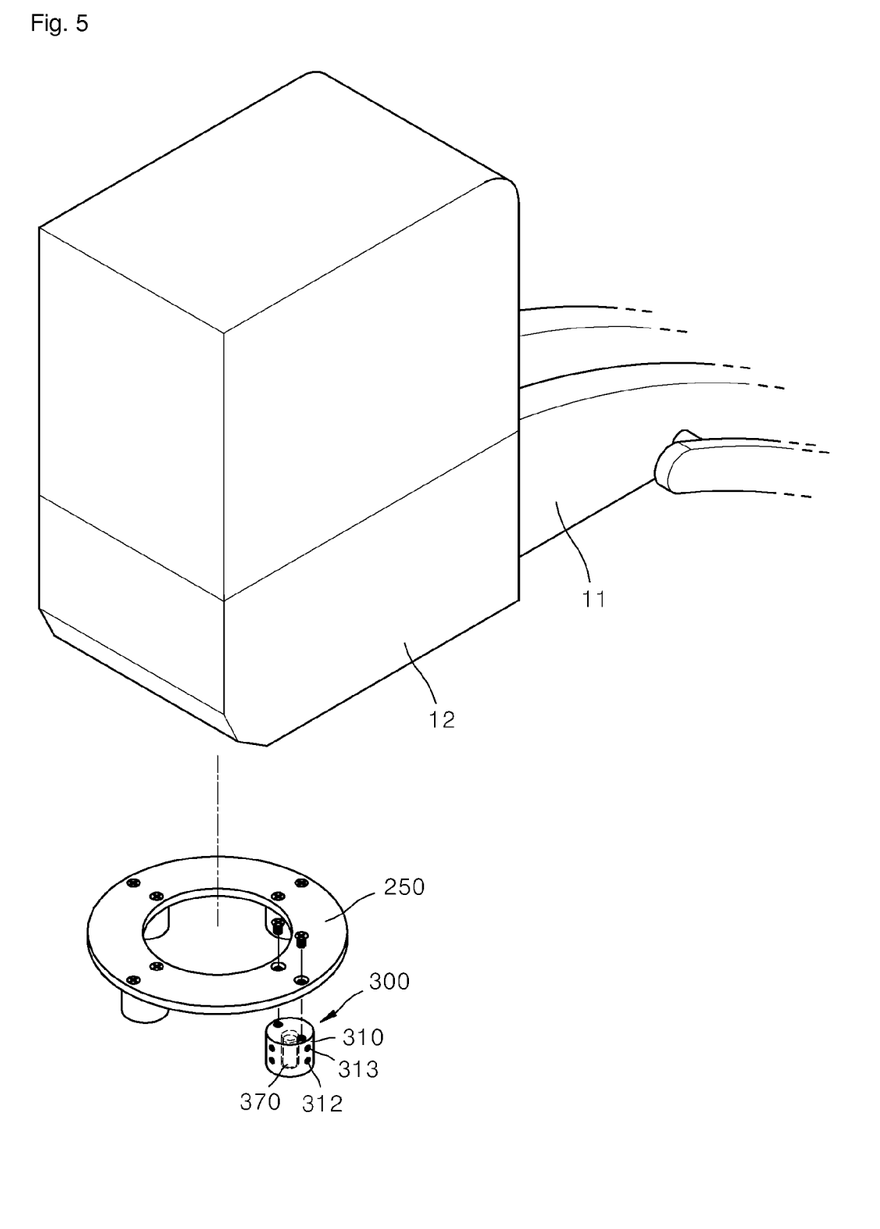
FIG. 5 is a perspective view of an X-ray targeting device according to another embodiment of the present invention.
Figure 6:
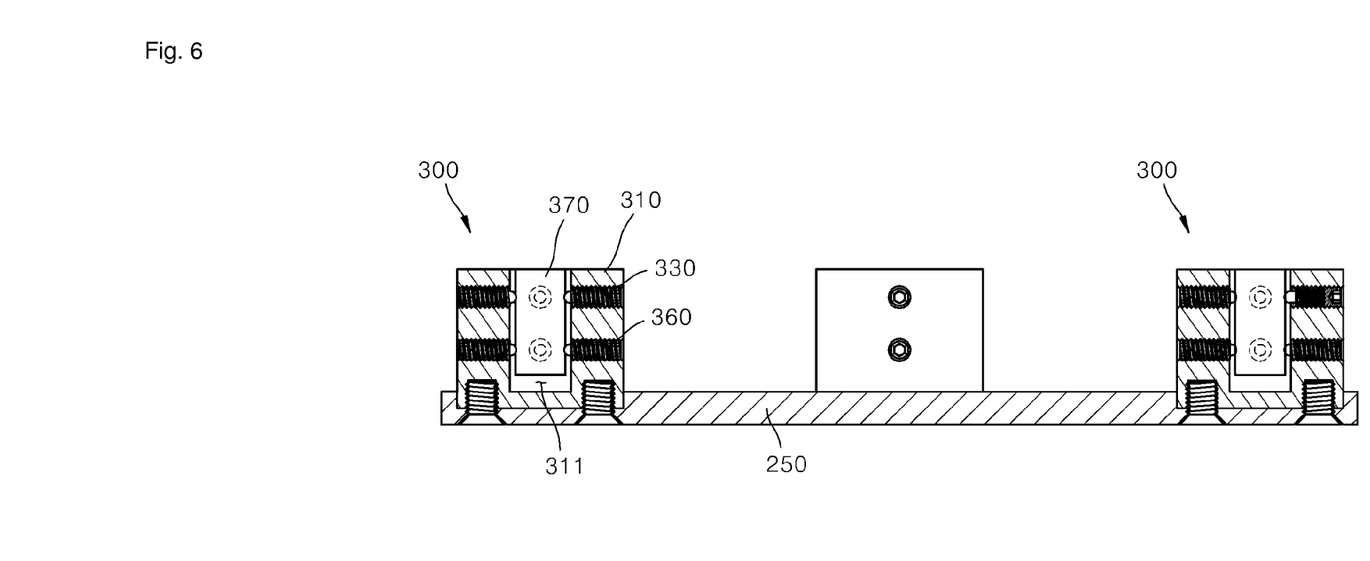
FIG. 6 is a cross-sectional view of the X-ray targeting device in FIG. 5.

Meanwhile, a frame 250 according to another embodiment of the present invention is illustrated in FIG. 5 and FIG. 6.

Elements which perform the same functions as in the previously illustrated drawings are marked with the same reference numerals.

Referring to the drawings, the frame 250 has a predetermined thickness, and is formed in a shape of a disk in which the through-hole 211 is formed at a central portion. The frame 250 has one side surface coming in contact with the X-ray generators and bolted to the X-ray generators by a coupling bolt. In addition, the plurality of light radiation units 300 are installed at the other side surface of the frame 250. The plurality of light radiation units 300 are installed to be spaced apart from each other in accordance with a circular virtual line having a predetermined radius with respect to the center of the through-hole 211.

Since the above-mentioned frame 250 has the light radiation units 300 installed to be exposed to the outside, a worker can easily manipulate the restraining members 330 and the pressing members 350.

Figure 7:
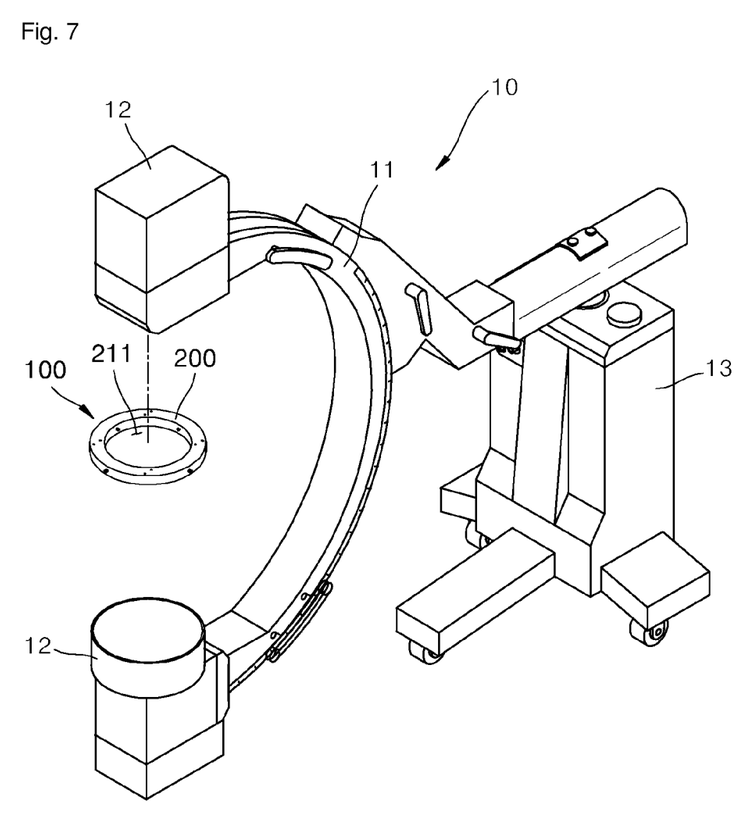
FIG. 7 is a perspective view of an X-ray targeting device according to still another embodiment of the present invention.
Figure 8:
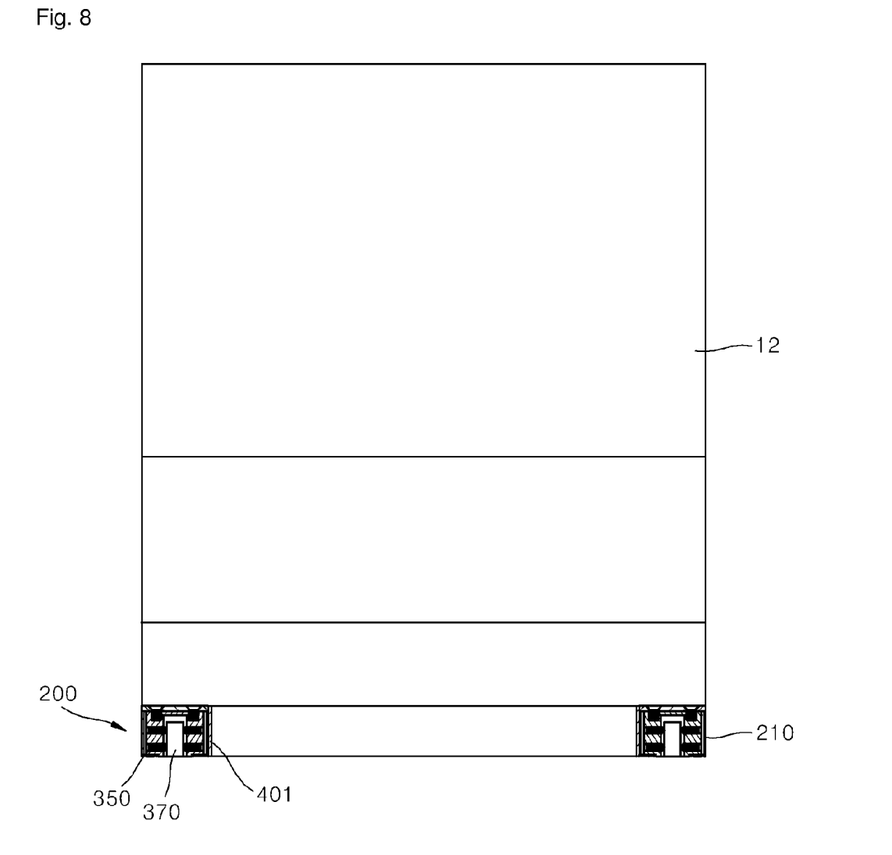
FIG. 8 is a cross-sectional view of the X-ray targeting device in FIG. 7.
Figure 9:
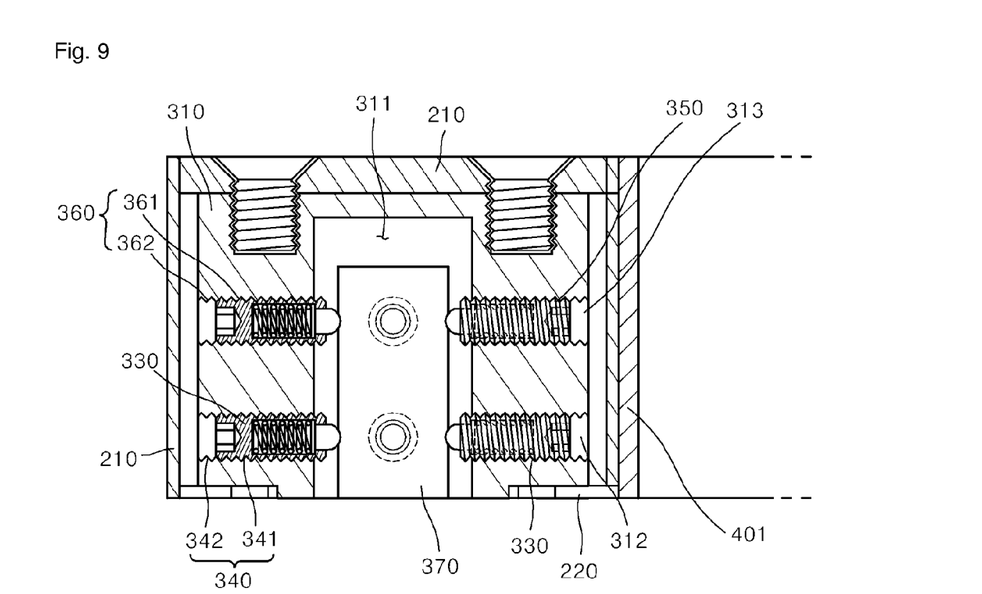
FIG. 9 is a cross-sectional view of a light radiation unit of the X-ray targeting device in FIG. 7.

Meanwhile, an X-ray targeting device according to still another embodiment of the present invention is illustrated in FIGS. 7 to 9.

Referring to the drawings, the X-ray targeting device further includes a shielding member 401 installed to surround an inner surface of the through-hole 211, and shielding X-rays radiated toward an inner surface of the frame 200 to limit the radiated range of the X-rays output from the X-ray generator 12.

The shielding member 401 is fixed to the inner surface of the through-hole 211 of the frame 200, and is formed in a ring shape in accordance with the inner surface of the frame 200. The shielding member 401 is formed to have a predetermined thickness from the inner surface of the frame 200 and a vertical width corresponding to the vertical length of the frame 200 to be able to cover the inner surface of the frame 200.

In addition, it is preferable that the shielding member 401 be formed of a material such as lead to be able to shield X-rays radiated toward the frame 200. As mentioned above, the shielding member 401 is installed to surround the inner surface of the frame 200 and shields the X-rays radiated toward the frame 200, thereby limiting the radiated range of the X-rays.

Figure 10:
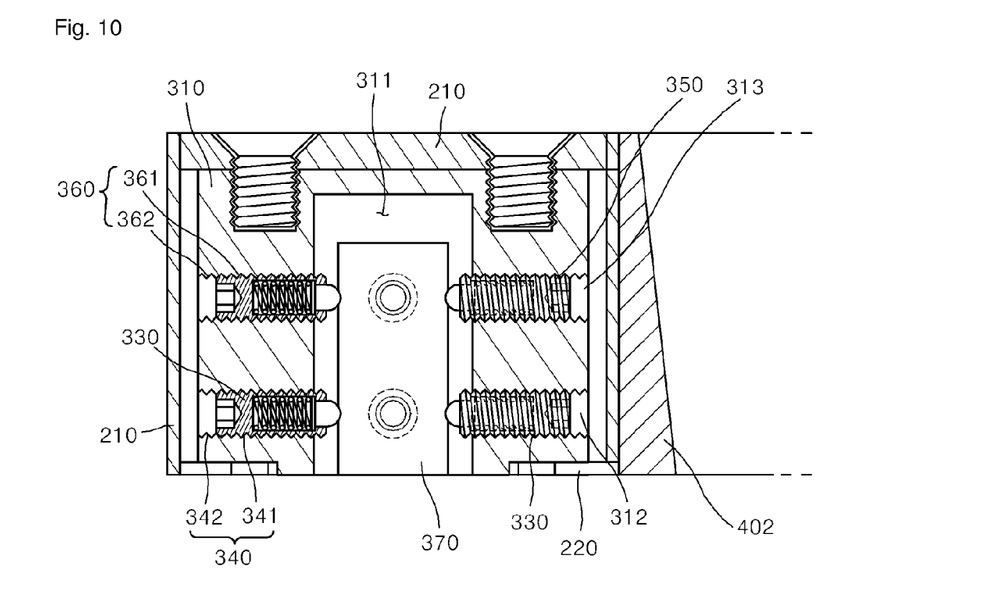
FIG. 10 is a cross-sectional view of a light radiation unit of an X-ray targeting device according to yet another embodiment of the present invention.

Meanwhile, a shielding member 402 according to yet another embodiment of the present invention is illustrated in FIG. 10.

Referring to the drawings, the shielding member 402 is formed such that a protruding length from the inner surface of the frame 200 further increases from an upper end portion abutting the X-ray generators to a lower end portion. Since a thickness of the shielding member 402 corresponding to an outlet side of the through-hole 211 of the frame 200 is greater than that corresponding to an inlet-side of the through-hole 211 of the frame 200 as mentioned above, the radiated range of the X-rays may be limited to be narrower. Since the thicknesses of the upper side and the lower side of the shielding member 402 are different from each other, the cost of materials is saved, such that the shielding member 402 may be manufactured with a relatively inexpensive cost.

Figure 11:
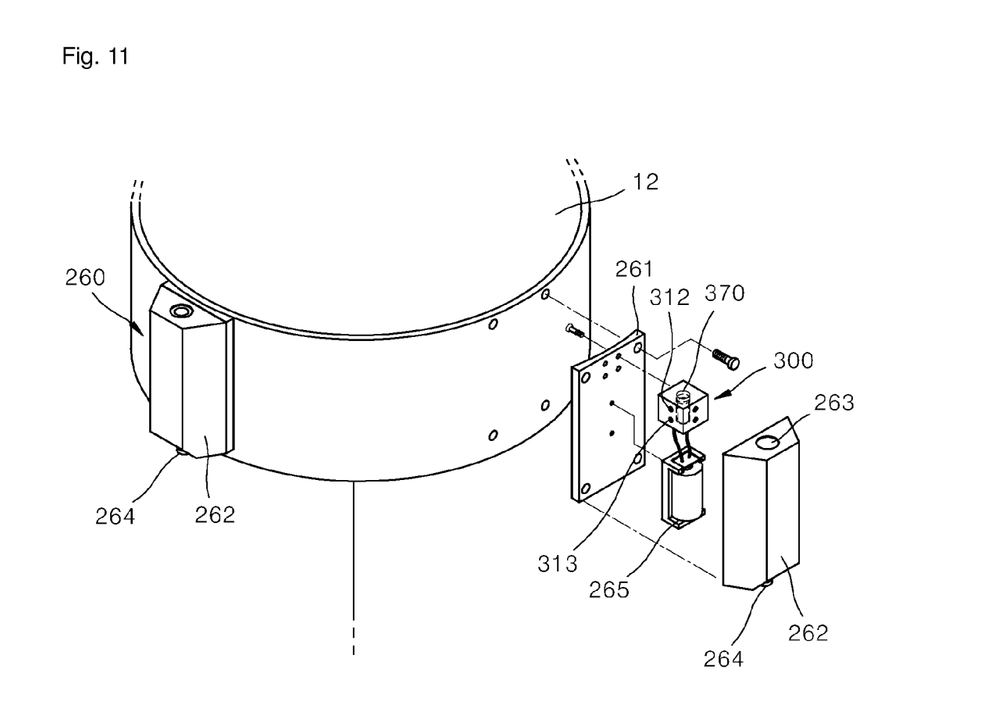
FIG. 11 is an exploded perspective view of an X-ray targeting device according to further another embodiment of the present invention.

Meanwhile, a frame 260 according to further another embodiment of the present invention is illustrated in FIG. 11.

Referring to the drawings, the frame 260 includes a plurality of fixing plates 261 spaced apart from each other in accordance with the circumferential direction at one outer circumferential surface of the X-ray generators 12, and having the light radiation units 300 installed at outer surfaces thereof, and a plurality of cover members 262 installed to cover the outer surfaces of the fixing plates 261 at which the light radiation units 300 are installed.

Inner surfaces of the fixing plates 261 which come in contact with the outer circumferential surface of the X-ray generators 12 are concavely formed to correspond to a curvature of the outer circumferential surface of the X-ray generators 12. The fixing plates 261 are bolted to the X-ray generators 12 by the fixing bolts. The light radiation units 300 are fixed to upper end portions of the outer surfaces of the fixing plates 261.

Here, the laser generator 370 of the light radiation units 300 radiates a laser forming a predetermined line to the X-ray generators 12 at the opposite side. Meanwhile, it is preferable that the laser generator 370 of the light radiation units 300 installed at the fixing plates 261 be set such that lasers radiated to the X-ray generators 12 at the opposite side cross with each other.

In addition, a battery 265 for supplying electricity to the light radiation units 300 is installed at outer surfaces of lower sides of the fixing plates 261 with respect to the light radiation units 300.

The cover members 262 have an insertion space provided to have the light radiation units 300 and the battery 265 inserted thereinto, and have side surfaces facing the outer surfaces of the fixing plates 261 formed to be open. A radiation hole 263 is formed at upper portions of the cover members 262 to enable a laser generated from the light radiation units 300 to penetrate therethrough. In addition, a switch 264 is installed at lower portions of the cover members 262 to selectively supply or block power to and from the light radiation units 300.

According to the present invention, since an X-ray targeting device includes a light radiation unit radiating guide light in accordance with a radiated direction of X-rays, a worker can easily identify the radiated direction or a radiated range of the X-rays, thereby saving time and effort required for X-ray imaging.

In addition, the present invention includes a shielding member installed at an inner surface of a through-hole of a frame through which X-rays pass and able to shield the X-rays radiated toward the frame, thereby preventing the worker from a disease caused by the X-rays.

Although the present invention has been described with reference to embodiments illustrated in the drawings, the embodiments are merely for illustrative purposes, and those of ordinary skill in the art will understand that various modifications and equivalent embodiments are possible from the embodiments.

Therefore, the actual scope of the present invention should be defined only by the attached claims.

What is claimed is:

1. An X-ray targeting device comprising:
    a frame installed at an X-ray generator of an X-ray imaging device which outputs X-rays toward a patient to be measured; and
    a light radiation unit installed at the frame, and configured to radiate guide light in accordance with a direction in which the X-rays are output to display a radiated position or radiated range of the X-rays with respect to the patient,
    wherein the light radiation unit comprises:
    a housing installed at the frame, configured to have an inner space provided inside, and configured to have an opening, which comes in communication with the inner space, formed at a side surface facing the patient;
    a laser generator inserted into the inner space and configured to radiate the guide light through the opening; and
    a restraining unit installed at the housing, configured to support the laser generator to prevent the laser generator from being separated from the housing, and configured to change a supported state of the laser generator with respect to the housing to be able to adjust a direction in which the guide light is radiated,
    wherein the restraining unit comprises:
    a plurality of restraining members respectively installed at inner surfaces of the housing which face each other with respect to a center line of the opening to move back and forth toward and from the inner space to have end portions come in contact with the laser generator inserted into the inner space;

first adjustment parts provided at the restraining members and the housing, and configured to adjust protruding lengths of pressing members from the inner surfaces of the housing to enable the restraining members to grip the laser generator;

a plurality of the pressing members respectively installed at inner surfaces of the housing at positions spaced apart from the restraining members in accordance with a longitudinal direction of the center line of the opening to move back and forth toward and from the inner space; and second adjustment parts provided at the restraining members and the housing, and configured to adjust the protruding lengths of the pressing members from the inner surfaces of the housing to be able to tilt the laser generator restrained by the restraining members by a predetermined angle, wherein the plurality of restraining members have the end portions, which come in contact with the laser generator, formed in semi-spherical shapes to enable the laser generator to be supported to be easily tilted by the pressing members, and the laser generator has insertion grooves formed in semi-spherical shapes to correspond to the end portions of the restraining members to have the restraining members respectively inserted into outer circumferential surfaces at positions facing the restraining members.

2. The X-ray targeting device according to claim 1, wherein the plurality of the pressing members are installed to be spaced apart from each other in accordance with a circumferential direction at the inner surfaces of the housing.

3. The X-ray targeting device according to claim 2, wherein the restraining members have the end portions, which come in contact with the laser generator, formed in semi-spherical shapes to enable the laser generator to be supported to be easily tilted by the pressing members, and the laser generator has insertion grooves formed in semi-spherical shapes to correspond to the end portions of the restraining members to have the restraining members respectively inserted into outer circumferential surfaces at positions facing the restraining members.

4. The X-ray targeting device according to claim 1, wherein the frame has a through-hole formed to enable the X-rays output from the X-ray generator to pass therethrough, and the plurality of the light radiation units are installed at the frame to be spaced apart from each other with respect to a center of the through-hole in accordance with a circular virtual line having a greater diameter than an inner diameter of the through-hole.

5. The X-ray targeting device according to claim 4, further comprising a shielding member installed to surround an inner surface of the through-hole, and configured to shield the X-rays radiated toward an inner surface of the frame to limit the radiated range of the X-rays output from the X-ray generator.

\* \* \* \* \*